(12) United States Patent
Arni (10) Patent No.: US 8,192,199 B2
(45) Date of Patent: Jun. 5, 2012

(54) DENTAL IMPLANT FOR IMPLANTING AN ARTIFICIAL TOOTH ON THE ANTERIOR PORTION OF THE MANDIBLE OF A PATIENT

(76) Inventor: Uri Arni, Beer Yaacov (IL)

( * ) Notice: Subject to any disclaimer, the term of this patent is extended or adjusted under 35 U.S.C. 154(b) by 392 days.

(21) Appl. No.: 12/515,226

(22) PCT Filed: Nov. 14, 2007

(86) PCT No.: PCT/IL2007/001418
§ 371 (c)(1),
(2), (4) Date: Nov. 5, 2009

(87) PCT Pub. No.: WO2008/059507
PCT Pub. Date: May 22, 2008

(65) Prior Publication Data
US 2010/0055644 A1   Mar. 4, 2010

Related U.S. Application Data

(60) Provisional application No. 60/859,349, filed on Nov. 15, 2006.

(51) Int. Cl.
*A61C 8/00* (2006.01)
(52) U.S. Cl. ...................................................... 433/174
(58) Field of Classification Search .......... 433/172–176, 433/167, 169, 220, 221, 225; 606/65, 300, 606/301, 305, 306; 411/411, 413, 397, 2; *A61C 13/263, 13/265, 13/267, 13/271, 13/273, A61C 13/225*
See application file for complete search history.

(56) References Cited

U.S. PATENT DOCUMENTS

| 2,892,226 | A | * | 6/1959 | Bradney ........................ 403/343 |
| 3,664,226 | A | * | 5/1972 | Gonzalez ......................... 411/2 |
| 4,053,982 | A | * | 10/1977 | Weissman ..................... 433/225 |
| 4,838,264 | A | * | 6/1989 | Bremer et al. ................ 606/104 |
| 4,872,840 | A | * | 10/1989 | Bori .............................. 433/173 |
| 5,816,809 | A |   | 10/1998 | Sapkos |
| 6,030,162 | A | * | 2/2000 | Huebner ...................... 411/413 |
| 6,048,204 | A | * | 4/2000 | Klardie et al. ................ 433/174 |
| 6,375,465 | B1|   | 4/2002 | Engman et al. |
| 6,695,616 | B2| * | 2/2004 | Ellison ......................... 433/174 |

(Continued)

OTHER PUBLICATIONS

"PCT Application No. PCT/IL2007/001418, International Search Report", (Mar. 18, 2008), 5 pgs.

(Continued)

*Primary Examiner* — Todd Manahan
*Assistant Examiner* — Tatiana Nobrega
(74) *Attorney, Agent, or Firm* — Shichrur & Co.

(57) ABSTRACT

Device for coupling an artificial tooth to a jawbone of a patient, the device including a dental implant, and a deformably removable nut, the dental implant including a threaded bone engaging portion, for engaging the dental implant with the jawbone, and a threaded assembly stage portion, for enabling screwing of the dental implant into the jawbone, and for coupling the artificial tooth with the jawbone, the deformably removable nut including a plurality of engagement features, and a nut disintegration feature, the engagement features enabling engagement of the nut with a tool, for screwing the nut on the dental implant, and for further screwing the dental implant in the jawbone, with the aid of the nut, the nut disintegration feature enabling removal of the nut from the dental implant, without unscrewing the nut from the threaded assembly stage portion.

28 Claims, 11 Drawing Sheets

U.S. PATENT DOCUMENTS

| | | | |
|---|---|---|---|
| 7,699,613 B2 * | 4/2010 | Niznick | 433/174 |
| 2003/0054318 A1 | 3/2003 | Gervais et al. | |
| 2006/0172258 A1 * | 8/2006 | Niznick | 433/174 |
| 2007/0099151 A1 * | 5/2007 | Ilan et al. | 433/173 |
| 2010/0203476 A1 * | 8/2010 | Studer et al. | 433/173 |
| 2010/0216093 A1 * | 8/2010 | Krush et al. | 433/174 |

OTHER PUBLICATIONS

"PCT Application No. PCT/IL2007/001418, Written Opinion of the International Searching Authority", (Mar. 18, 2008), 7 pgs.

* cited by examiner

VIEW II

FIG. 3B

III-III

DENTAL IMPLANT FOR IMPLANTING AN ARTIFICIAL TOOTH ON THE ANTERIOR PORTION OF THE MANDIBLE OF A PATIENT

RELATED APPLICATIONS

This application is a national stage application under 35 U.S.C. §371 of PCT/IL2007/001418, filed Nov. 14, 2007, and published as WO 2008/059507 A1 on May 22, 2008, which claims priority under 35 U.S.C. §119 to U.S. application Ser. No. 60/859,349, filed Nov. 15, 2006, which applications and publication are incorporated herein by reference and made a part hereof in their entirety.

FIELD OF THE DISCLOSED TECHNIQUE

The disclosed technique relates to medical devices in general, and to dental implants, in particular.

BACKGROUND OF THE DISCLOSED TECHNIQUE

Methods for implanting artificial teeth are known in the art. The incisors of the upper jaw (i.e., the upper jaw incisors) articulate with those of the mandible (i.e., the mandibular incisors). In a normal human being the upper jaw incisors and the mandibular incisors usually protrude at an oblique angle relative to both the upper jaw and the mandible, respectively. Following is a description of an exemplary method for implanting an artificial incisor, as known in the art.

The dental surgeon employs a dental screw, an angled abutment, and a fastening screw. The angled abutment is slanted with respect to the dental screw, in order to match the inclination of the neighboring teeth (which are slanted with respect to the jawbone), while the dental screw is to be aligned with the jawbone. In this manner, the inclination of the artificial incisor is matched with that of the anatomical incisor, and proper articulation of the artificial incisor with the adjacent incisors is provided. The dental screw has an external thread at one end thereof, for screwing into the jawbone. The other end of the dental screw has a hexagonal depression and an internal thread whose major diameter is smaller than the width of the hexagonal depression. The abutment has a hexagonal protrusion at one end thereof, and a through hole which passes through the hexagonal protrusion. The hexagonal protrusion of the abutment matches the hexagonal depression in the dental screw. The dental surgeon screws the dental screw in the jawbone, aligns the angled orientation of the abutment relative to the adjacent angled teeth when inserting the hexagonal protrusion in the hexagonal depression, and fastens the abutment to the dental screw by screwing the fastening screw in the internal thread of the dental screw, through the hole of the abutment. The dental surgeon, then assembles or fastens the artificial incisor, which has a blind hole therein, to the abutment, such as by an adhesive.

The method described herein above is applicable to cases in which the major diameter of the dental screw is approximately 3.75 mm or larger (i.e., relatively thick upper jaw bones or mandibles). Employment of a dental screw having a major diameter of less than 3.75 mm is either impractical or unsafe, because the wall thickness of the dental screw in the region of the internal thread is not sufficient to provide the mechanical strength necessary to fasten the abutment to the dental screw, lest ensuring long term use of the artificial incisor by the patient.

SUMMARY OF THE DISCLOSED TECHNIQUE

It is an object of the disclosed technique to provide a novel method and system for implanting an artificial tooth.

In accordance with the disclosed technique, there is thus provided a device for coupling an artificial tooth to a jawbone of a patient. The device includes a dental implant, and a deformably removable nut. The dental implant includes a threaded bone-engaging portion, for engaging the dental implant with the jawbone, and a threaded assembly-stage portion, for enabling screwing of the dental implant into the jawbone, and for coupling the artificial tooth with the jawbone. The deformably removable nut includes a plurality of engagement features, and a nut-disintegration feature.

The engagement features enable engagement of the nut with a tool, for screwing the nut on the dental implant, and for further screwing the dental implant in the jawbone, with the aid of the nut. The nut-disintegration feature enables removal of the nut from the dental implant, without unscrewing the nut from the threaded assembly-stage portion.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a dental implant having an external thread, and a deformably removable nut for implanting the dental implant in a jawbone of a patient. The nut includes one or more external grooves cut on an external wall thereof, thereby reducing the thickness of the wall there along, for facilitating deformation of the nut and enabling its removal from the dental implant, without unscrewing the nut from the dental implant. Unscrewing of the nut from the dental implant may also exert unscrewing torque on the dental implant, which can dislodge the dental implant from the jawbone. In an embodiment of the disclosed technique, the nut features one or more internal grooves cut in proximity to the external grooves, on a periphery of the nut wall, thus further reducing the thickness of the wall along the grooves. In other words, the internal grooves and the external grooves are located at such proximity to one another, that the wall thickness of the nut between each pair of the internal groove and the external groove, is smaller than that between the inner wall and the periphery. This relatively small wall thickness enables fracturing and removal of the nut from the external thread of the dental implant, without necessitating the unscrewing of the nut.

For example, by shattering the nut with the aid of a pointed tool which fits the external nut-disintegration features, or by breaking the nut at one of the external nut-disintegration features with the aid of the pointed tool, and opening apart the nut. The nut further includes a plurality of engagement features for screwing the nut on the external thread of the dental implant, with the aid of a nut screwing tool.

The external thread of the dental implant includes a bone engaging portion and an assembly stage portion. A dental surgeon screws the nut on the assembly stage portion until the nut stops turning before reaching the bone engaging portion. The dental surgeon continues to turn the nut in the same direction, to screw the bone engaging portion of the dental implant in the jawbone, and to implant the dental implant in the jawbone. The dental surgeon removes the nut from the assembly stage portion, by breaking it, and screws an artificial tooth coupler having an internal thread, on the assembly stage portion. The dental surgeon can fasten an artificial tooth to the artificial tooth coupler, for example by employing an adhesive, tightening means, and the like.

Figure 1:
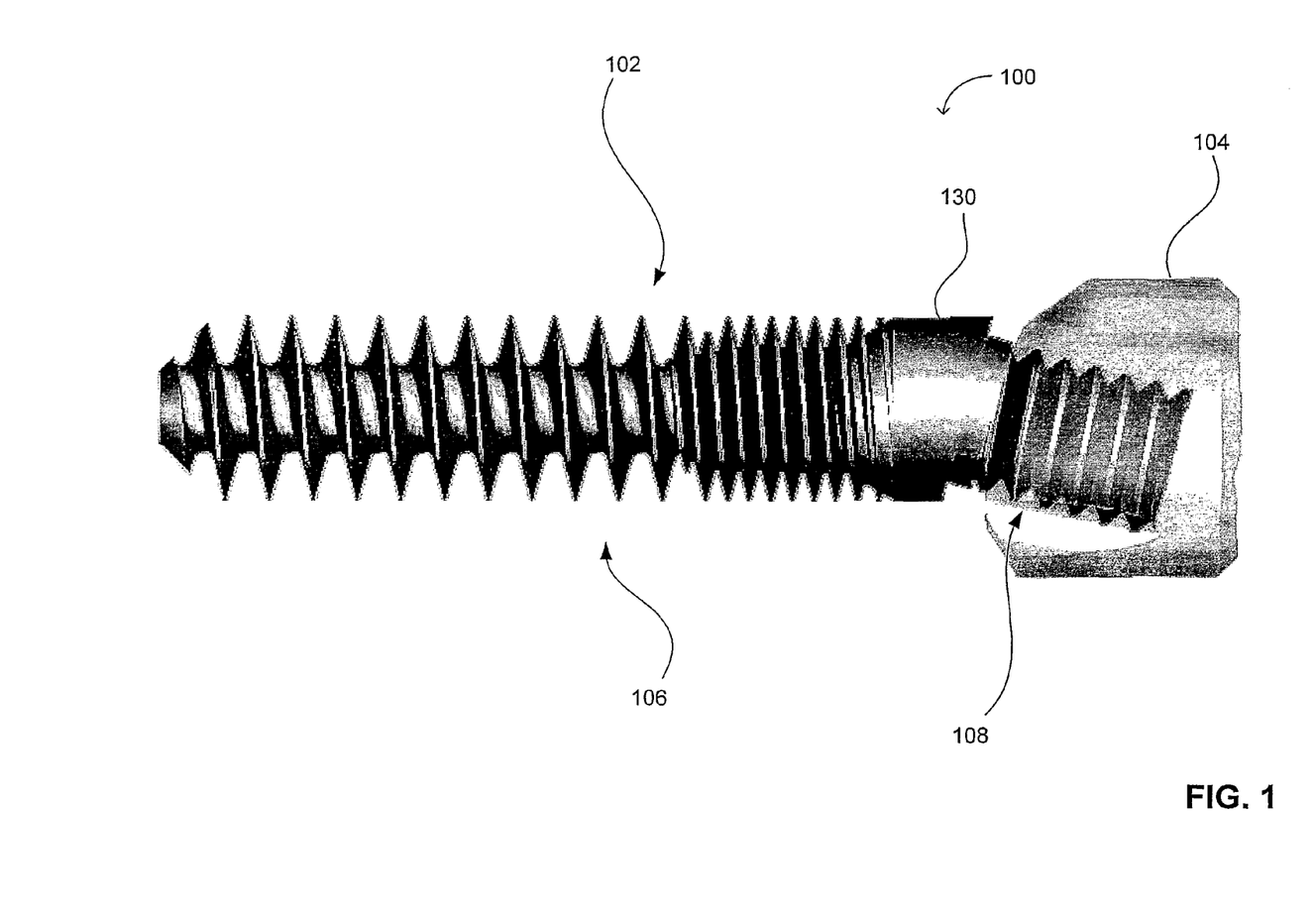
FIG. 1 is a schematic illustration of a device, for implanting an artificial incisor in the jawbone of a patient, constructed and operative according to an embodiment of the disclosed technique.
Figure 2A:
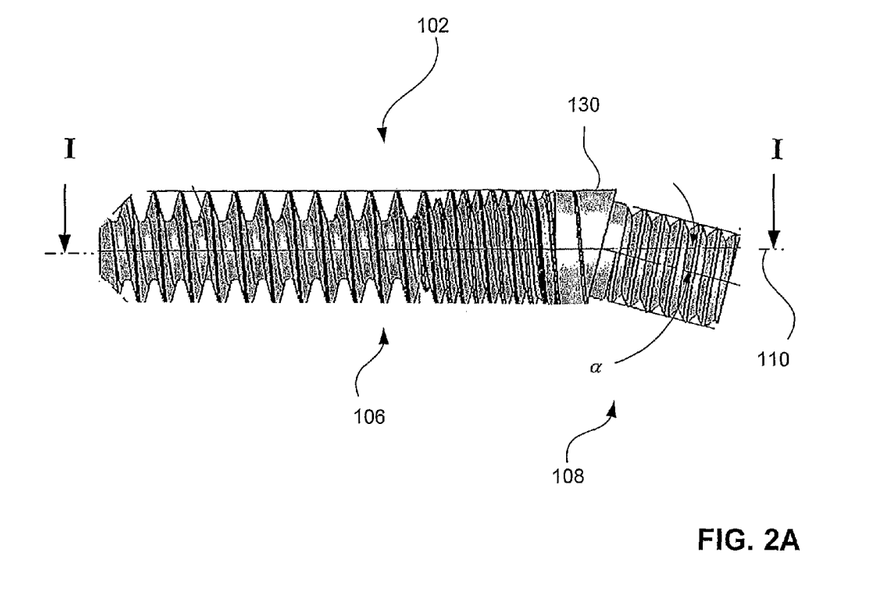
FIG. 2A is a schematic illustration of the dental implant of the device of FIG. 1.
Figure 2B:
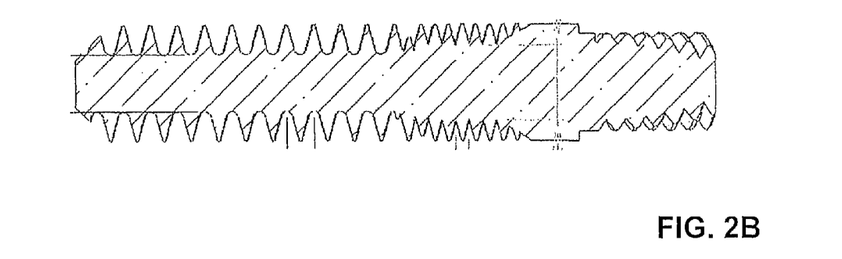
FIG. 2B is a schematic illustration of a cross section of the dental implant of FIG. 2A.
Figure 3A:
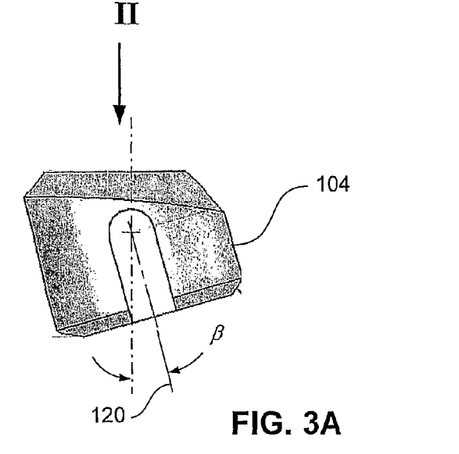
FIG. 3A is a schematic illustration of the deformably removable nut of the device of FIG. 1.
Figure 3B:
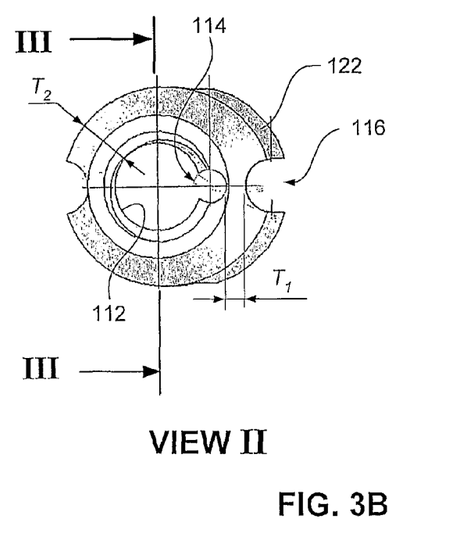
FIG. 3B is a schematic illustration of a top view of the deformably removable nut of FIG. 3A.
Figure 3C:
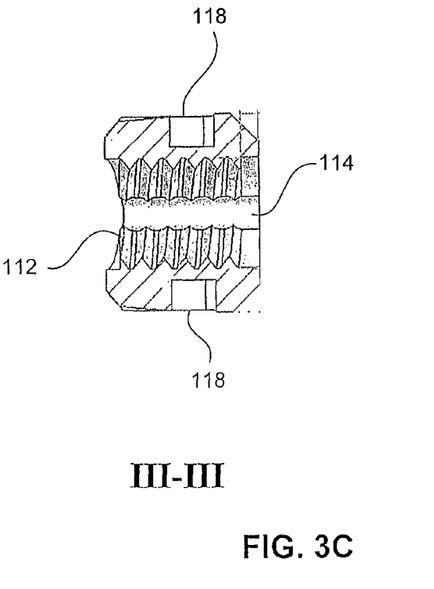
FIG. 3C is a schematic illustration of a section of the deformably removable nut of FIG. 3B.
Figure 4A:
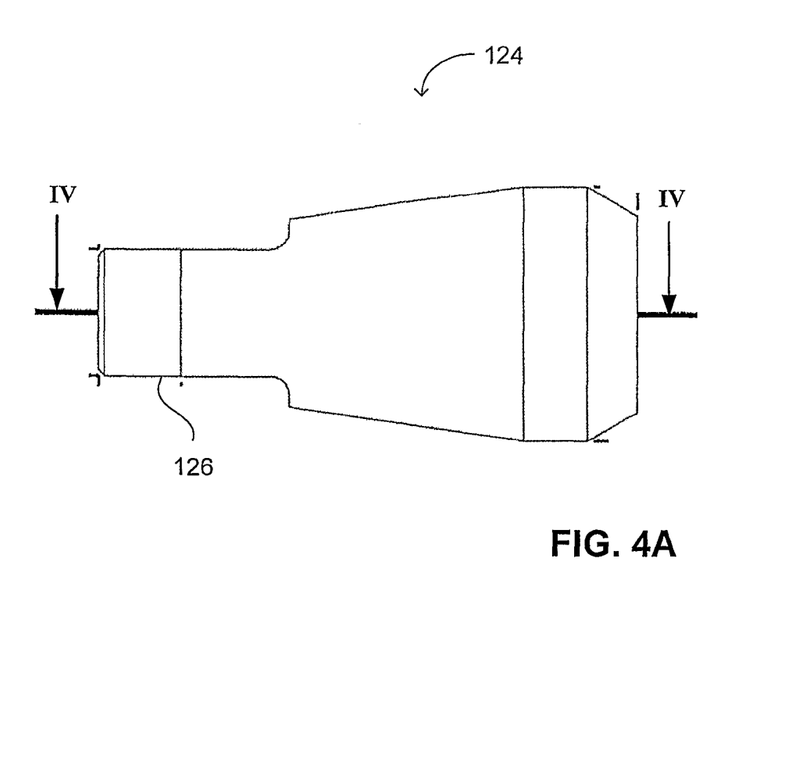
FIG. 4A is a schematic illustration of an artificial tooth coupler for coupling an artificial incisor with the assembly stage portion of the external thread of the dental implant of FIG. 2A.
Figure 4B:
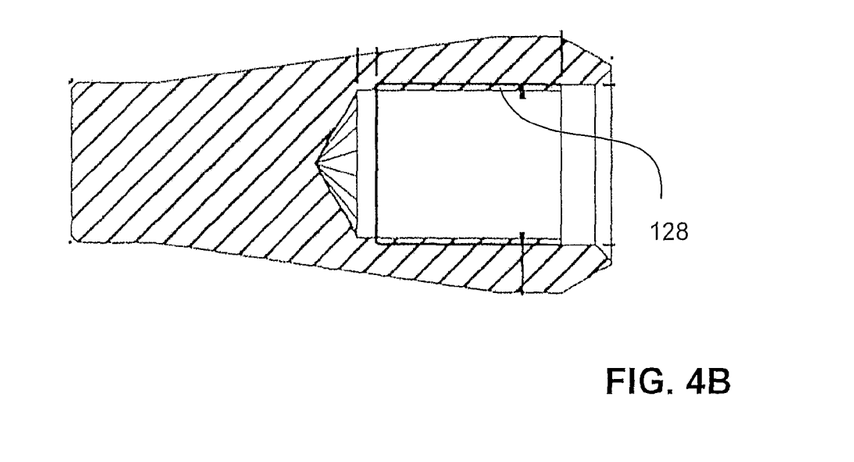
FIG. 4B is a schematic illustration of a section of the artificial tooth coupler of FIG. 4A.
Figure 5:
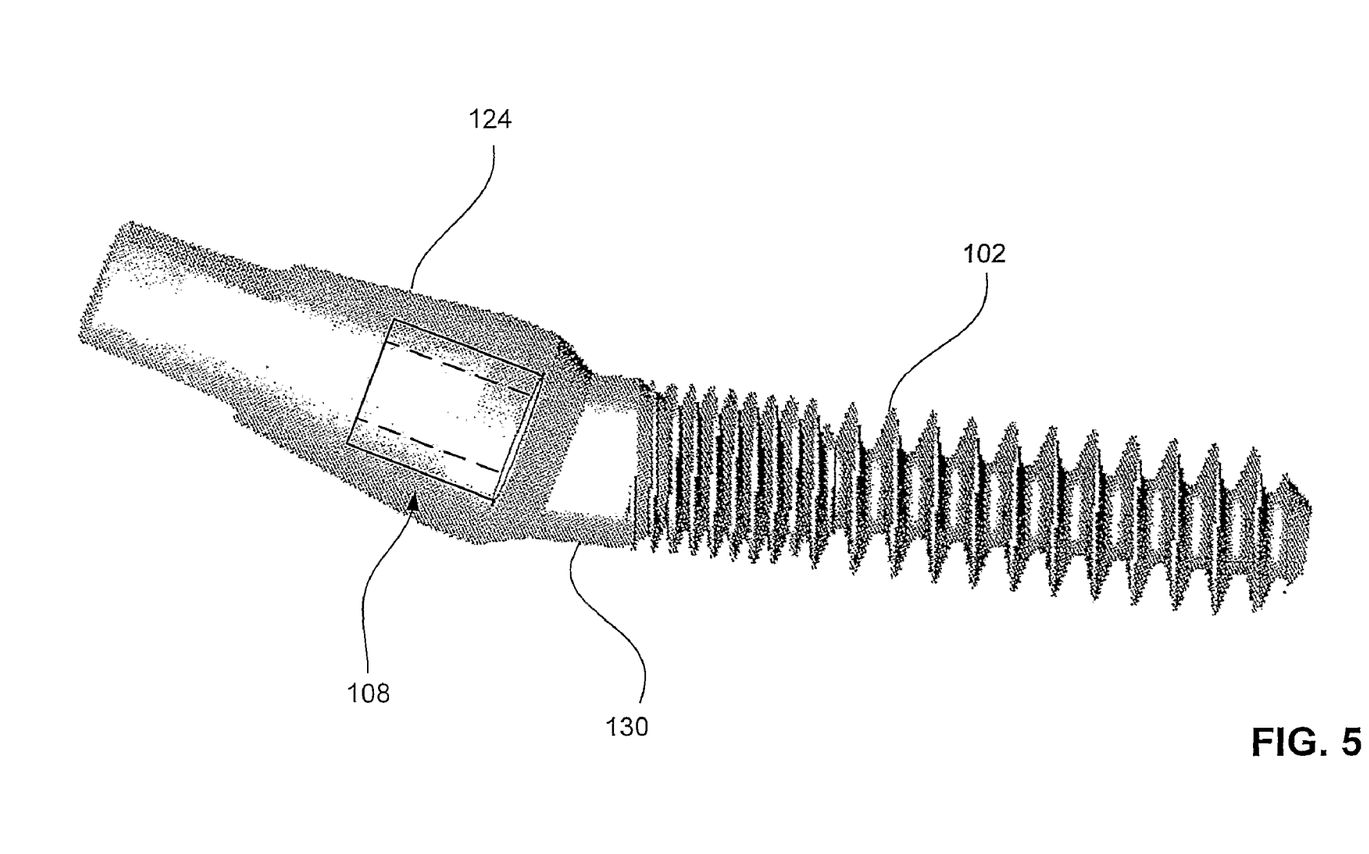
FIG. 5 is a schematic illustration of a perspective view of the artificial tooth coupler of FIG. 4A, screwed on the assembly stage portion of the dental implant of FIG. 2A.

Reference is now made to FIGS. 1, 2A, 2B, 3A, 3B, 3C, 4A, 4B, and 5. FIG. 1 is a schematic illustration of a device generally referenced 100, for implanting an artificial incisor in the jawbone of a patient, constructed and operative according to an embodiment of the disclosed technique. FIG. 2A is a schematic illustration of the dental implant of FIG. 1. FIG. 2B is a schematic illustration of a cross section (i.e., cross section I) of the dental implant of FIG. 2A. FIG. 3A is a schematic illustration of the deformably removable nut of the device of FIG. 1. FIG. 3B is a schematic illustration of a top view (i.e., view II) of the deformably removable nut of FIG. 3A. FIG. 3C is a schematic illustration of a section (i.e., section III) of the deformably removable nut of FIG. 3B. FIG. 4A is a schematic illustration of an artificial tooth coupler for coupling an artificial incisor with the assembly stage portion of the external thread of the dental implant of FIG. 2A. FIG. 4B is a schematic illustration of a section (i.e., section IV) of the artificial tooth coupler of FIG. 4A. FIG. 5 is a schematic illustration of a perspective view of the artificial tooth coupler of FIG. 4A, screwed on the assembly stage portion of the dental implant of FIG. 2A.

With reference to FIGS. 1, 2A, and 2B, device 100 includes a dental implant 102 and a deformably removable nut 104. Dental implant 102 includes a bone engaging portion 106 and an assembly stage portion 108. Bone engaging portion 106 is in form of an external thread as described herein below, with reference to FIGS. 6A, 6B, 7A, and 7B. Bone engaging portion 106 is constructed in order to provide firm engagement of dental implant 102 with a jawbone (not shown) of a patient (not shown), by screwing dental implant 102 in the jawbone. Assembly stage portion 108 is in form of an external thread. Assembly stage portion 108 is slanted at a predetermined angle $\alpha$ from a longitudinal axis 110 (FIG. 2A) of bone engaging portion 106. The thread profile of assembly stage portion 108 is different than that of bone engaging portion 106. Alternatively, the thread profile of assembly stage portion 108 is substantially the same as that of bone engaging portion 106.

With reference to FIGS. 3A, 3B, and 3C, deformably removable nut 104 includes an internal thread 112, an internal nut-disintegration feature 114, an external nut-disintegration feature 116, and a plurality of engagement features 118. In the example set forth in FIGS. 3A, 3B, and 3C, each of internal nut-disintegration feature 114 and external nut-disintegration feature 116 is in form of a longitudinal depression. Each of internal nut-disintegration feature 114 and external nut-disintegration feature 116 can be in form of a groove, a notch, or a polygonal depression such as triangle or hexagon, and the like. Alternatively, other features that allow the fracturing of the wall of the nut, may be implemented, such as a set of depressions that form a perforated line in the wall, a set of through holes or slits that form openings in the wall of the nut, and the like.

Each of internal nut-disintegration feature 114 and external nut-disintegration feature 116 runs from a distal end of deformably removable nut 104, to a proximal end thereof, substantially along a longitudinal axis 120 of deformably removable nut 104. Alternatively, each of internal nut-disintegration feature 114 and external nut-disintegration feature 116 runs from the distal end to the proximal end, along an axis inclined to longitudinal axis 120.

The nut-disintegration feature can be implemented in various forms. For example, in case the deformably removable nut is made of a polymer (e.g., plastic, Nylon, Teflon®), the deformably removable nut can be disintegrated and removed from the assembly stage portion, by applying a chemical substance which reacts with the deformably removable nut, and partially or entirely dissolves the deformably removable nut. Alternatively, the plastic deformably removable nut can be disintegrated by applying heat for example, by employing a heat probe, laser beam, and the like.

Internal thread 112 is inclined from longitudinal axis 120, by an angle $\beta$, where $\beta$ is approximately equal to $\alpha$ (FIG. 2A). Internal nut-disintegration feature 114 is in form of a groove in internal thread 112 along longitudinal axis 120. External nut-disintegration feature 116 is in form of a groove on an outer surface 122 of deformably removable nut 104, along longitudinal axis 120. A first wall thickness $T_1$ is defined between internal nut-disintegration feature 114 and external nut-disintegration feature 116. A second wall thickness $T_2$ characterizes deformably removable nut 104 in regions thereof, remote from internal nut-disintegration feature 114 and external nut-disintegration feature 116. It is noted that first wall thickness $T_1$ is smaller than second wall thickness $T_2$. Therefore, the dental surgeon can crack open deformably removable nut 104 while it is screwed on assembly stage portion 108, by entering a flat-tipped object, such as a screwdriver for a slotted flathead screw (not shown) into external nut-disintegration feature 116, and twisting the flat-tipped screwdriver slotted tip about a rotation axis (not shown), substantially perpendicular to longitudinal axis 120. In this manner, two sides of internal nut-disintegration feature 114 and external nut-disintegration feature 116 are pulled apart, and the thin wall between internal nut-disintegration feature 114 and external nut-disintegration feature 116 is broken.

It is noted that if the flat-tipped object is inserted into external nut-disintegration feature 116, internal nut-disintegration feature 114 can be eliminated, as long as the wall thickness along external nut-disintegration feature 116 is sufficiently small, in order to cause the breakage of deformably removable nut 104, with the aid of the flat-tipped object. Alternatively, external nut-disintegration features 116 can be eliminated if internal nut-disintegration features 114 are to be employed for the entering of a compatible pointed object that is customized for the breaking of the thin wall along internal nut-disintegration features 114 (for example, by the twisting of the pointed object against the sides of a internal nut-disintegration feature 114, or by the pulling apart of two opposing objects inserted in two opposing external nut-disintegration features 116, and the like).

Further alternatively, the deformably removable nut can include a plurality of internal nut-disintegration features and external nut-disintegration features, in form of longitudinal depressions, as described herein below in connection with FIG. 10C. Every pair of these internal nut-disintegration features and external nut-disintegration features are located at such a proximity, that the wall thickness of the deformably removable nut in region of the internal nut-disintegration features and the external nut-disintegration features, is smaller than those in other regions of the deformably removable nut. In this case, the dental surgeon can shatter the deformably removable nut in pieces, by operating the pointed tool on one or more of the external nut-disintegration features.

With reference to FIG. 3C, each of engagement features 118 is in form of a depression in outer surface 122, to facilitate screwing of deformably removable nut 104 on assembly stage portion 108, by employing a compatible screwing tool (not shown). Alternatively, each of engagement features 118 is in form of a protrusion on outer surface 122, whose size and location is compatible with those of the screwing tool.

With reference to FIGS. 4A, and 4B, an artificial tooth coupler 124 includes a protrusion 126 and an internal thread 128. The thread profile of internal thread 128 is compatible with that of assembly stage portion 108.

With reference to FIG. 1, the dental surgeon screws deformably removable nut 104 on assembly stage portion 108 with the aid of the screwing tool, until deformably removable nut 104 stops turning before reaching bone engaging portion 106. For this purpose, dental implant 102 can include a screw stop portion 130, which separates bone engaging portion 106 and assembly stage portion 108, in order to prevent screwing of deformably removable nut 104 on bone engaging portion 106. In case the thread profile of assembly stage portion 108 is different than that of bone engaging portion 106, screw stop portion 130 can be eliminated, since deformably removable nut 104 cannot be screwed on bone engaging portion 106, and since this feature alone, provides a stop to advancement of deformably removable nut 104 along bone engaging portion 106, past assembly stage portion 108. The stopping means may also be provided on the nut such as a stopping shoulder or a covering head of a crown nut.

When deformably removable nut 104 is screwed up to stop portion 126, deformably removable nut 104 can not be screwed any further on assembly stage portion 108. The dental surgeon, then screws bone engaging portion 106 in the jawbone, by employing deformably removable nut 104 and the screwing tool. In this manner, the dental surgeon implants dental implant 102 in the jawbone. The dental surgeon disengages deformably removable nut 104 from assembly stage portion 108, by employing the pointed tool, as described herein above.

With reference to FIG. 5, the dental surgeon screws artificial tooth coupler 124 on assembly stage portion 108 of dental implant 102. Finally, the dental surgeon can fasten an artificial incisor (not shown) to artificial tooth coupler 124, thereby completing the procedure of implanting the artificial incisor in the jawbone of the patient.

Dental implant 102 includes an assembly stage portion 108 which is in form of an external thread, rather than an internal thread, for engaging dental implant 102 with artificial tooth coupler 124. It is noted that such a configuration allows employment of a dental implant, which has a bone engaging portion, having a major diameter smaller than in the case of a bone engaging portion in form of an internal thread, but a larger thread length. This feature enables implant of a relatively small diameter dental implant (e.g., smaller than 3 mm), in a relatively thin jawbone.

It is further noted that inclination angle α from longitudinal axis 110 (FIG. 2A), enables implant of an artificial incisor in the jawbone, which is also inclined to the mandible at approximately an inclination angle α. It is noted that employment of deformably removable nut 104 whose internal thread 112 is slanted to longitudinal axis 120 at an angle β, enables turning of dental implant 102 about longitudinal axis 110, which is offset from assembly stage portion 106 by inclination angle α.

Figure 6A:
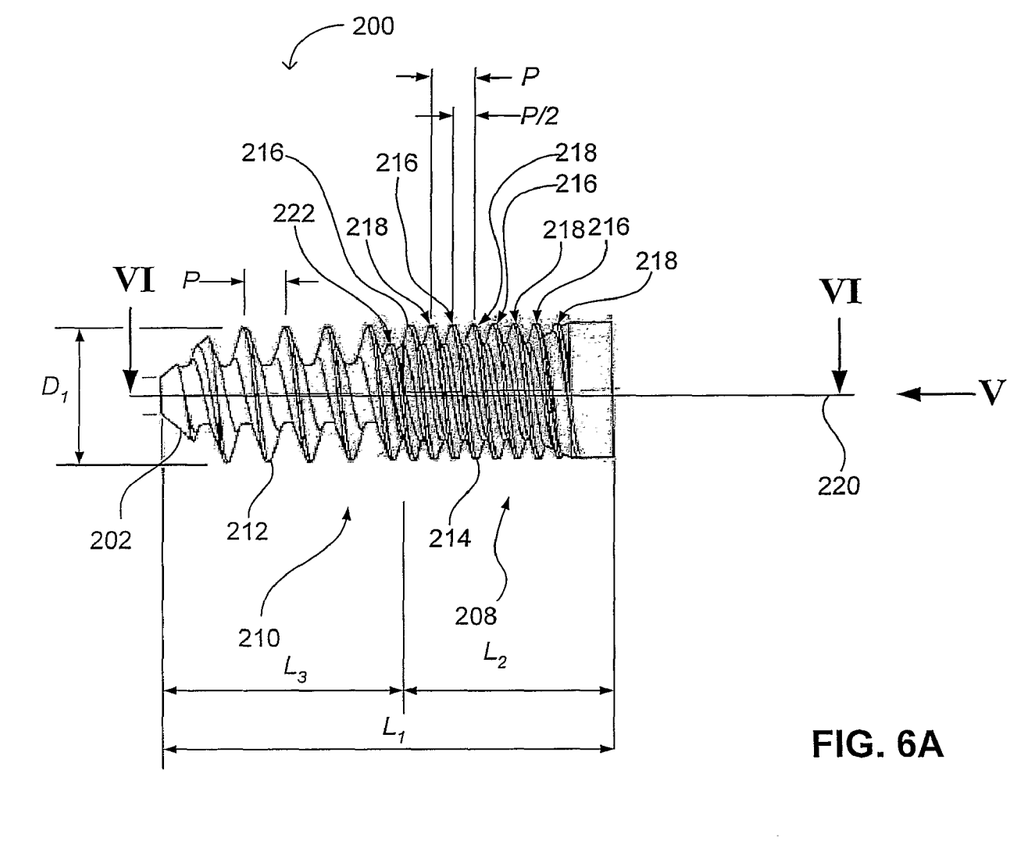
FIG. 6A is a schematic illustration of a dental implant, constructed and operative according to another embodiment of the disclosed technique.
Figure 6B:
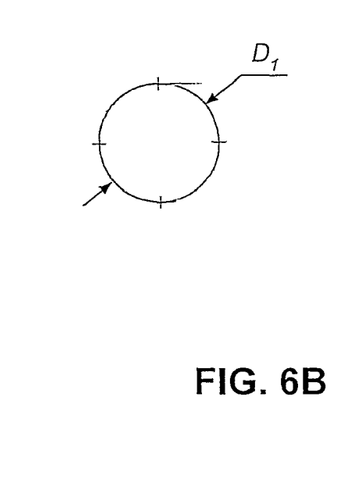
FIG. 6B is a schematic illustration of a side view of the dental implant of FIG. 6A.
Figure 7A:
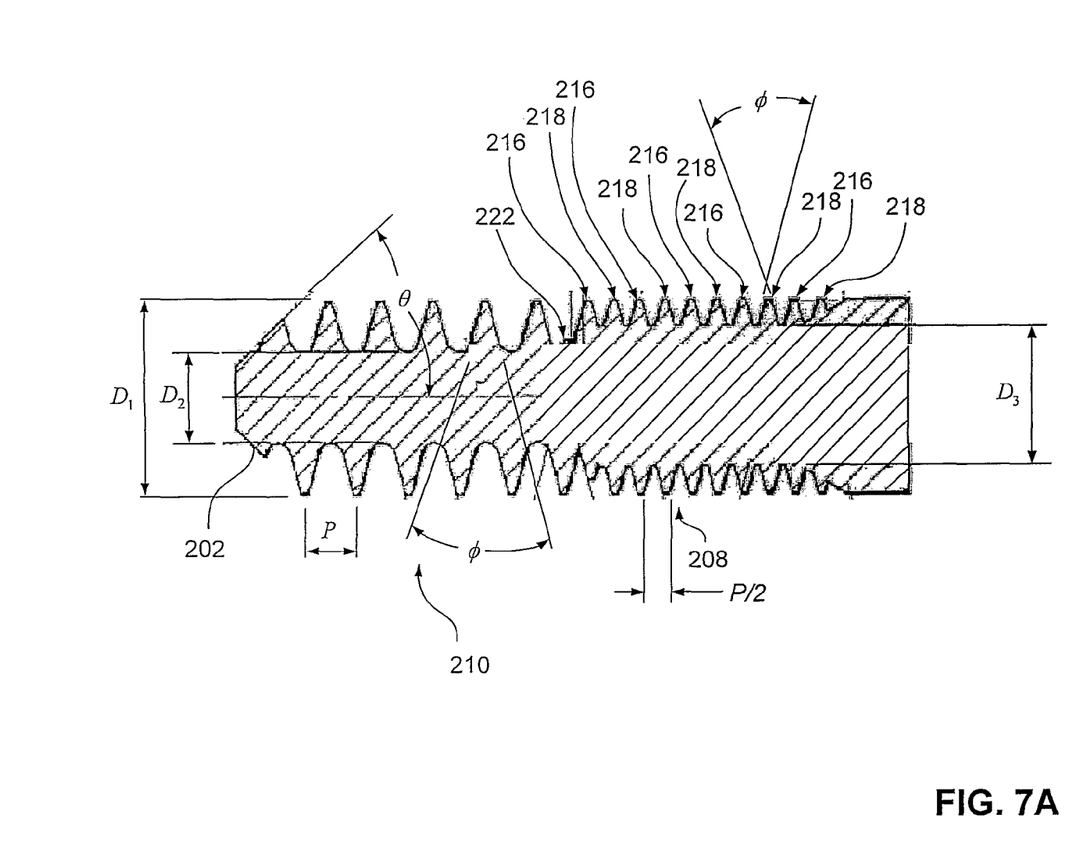
FIG. 7A is a schematic illustration of a longitudinal section of the dental implant of FIG. 6A.
Figure 7B:
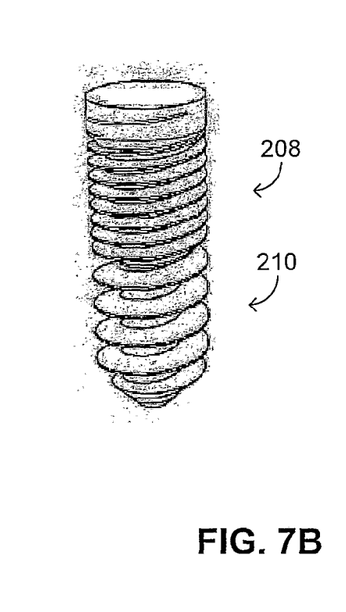
FIG. 7B is a schematic illustration of a perspective view of the dental implant of FIG. 6A.

Reference is now made to FIGS. 6A, 6B, 7A, and 7B. FIG. 6A is a schematic illustration of a dental implant generally referenced 200, constructed and operative according to another embodiment of the disclosed technique. FIG. 6B is a schematic illustration of a side view (view V) of the dental implant of FIG. 6A. FIG. 7A is a schematic illustration of a longitudinal section (section VI-VI) of the dental implant of FIG. 6A. FIG. 7B is a schematic illustration of a perspective view of the dental implant of FIG. 6A.

With reference to FIGS. 6A and 6B, dental implant 200 includes a finely threaded portion 208 (i.e., finely threaded dental implant proximal portion), and a coarsely threaded portion 210 (i.e., coarsely threaded dental implant distal portion). Finely threaded portion 208 is proximal to the outer part of the jawbone, where the artificial tooth is to be coupled to. Coarsely threaded portion 210 is at a distal end of dental implant 200. Finely threaded portion 208 is between 5 to 6.5 mm long, and coarsely threaded portion 210 is between 6.5 to 8 mm long, correspondingly, such that dental implant 200 is approximately 13 mm long.

Coarsely threaded portion 210 includes a distal end 202, which is an optional feature in form of a truncated cone tapering at an angle of θ, in order to facilitate self tapping of dental implant 200 into the jawbone of the patient. The screw thread along coarsely threaded portion 210 continues up to distal end 202. Distal end 202 is particularly short in order to avoid reduction of bonding area when dental implant 200 is subject to dislodging forces, and can be entirely eliminated, if such self tapping facilitation is redundant.

Finely threaded portion 208 has a minor diameter $D_3$ (FIG. 7A), which is greater than a minor diameter $D_2$ of coarsely threaded portion 210. Dental implant 200 is of a length $L_1$ and includes finely threaded portion 208 of a length $L_2$, and coarsely threaded portion 210 of a length $L_3$. Dental implant 200 further includes a primary thread 212 and one or more secondary threads 214. Primary thread 212 runs seamlessly along the entire length of dental implant 200, namely—along both finely threaded portion 208 and coarsely threaded portion 210. Primary thread 212 has a constant pitch P, and a major diameter $D_1$.

The value of major diameter $D_1$ is between 3.75 and 4.6 mm. The value of constant pitch P is between 1 and 1.3 mm. Primary thread 212 has a coarse thread height (not shown) in coarsely threaded portion 210, and a fine thread height (not shown) in finely threaded portion 208, wherein the coarse thread height is larger than the fine thread height. The value of the fine thread height is between 0.4 and 0.7 mm. The value of the coarse thread height is between 1 and 1.4 mm.

The coarse thread height defines a small minor diameter $D_2$ respective of primary thread 212. The fine thread height defines a large minor diameter $D_3$ respective of each of secondary threads 214, wherein $$D_3 > D_2 \quad (1)$$

It is noted that the greater the difference between major diameter $D_1$ and each of minor diameters $D_2$ and $D_3$, respectively, the greater is the thread height and the greater is the contact surface between dental implant 200 and the jawbone. This substantially large contact surface, has a significant role in resisting the tensile forces and the moments, which act on dental implant 200 especially during mastication. Therefore, this contact surface should be as large as possible.

In order to avoid moments and tensile forces which can damage dental implant 200 during the screwing operation within the jawbone, the pitch of each of secondary threads 214, substantially equals to pitch P of primary thread 212. Each of secondary threads 214 runs parallel to the primary thread 212, along finely threaded portion 208, at an offset. This offset equals to P/(n+1), where n=1,2,3 . . . N is the quantity of the secondary threads 214, which are manufactured in finely threaded portion 208. In case there is only one secondary thread 214, n=1, the offset equals to half of the pitch P.

Preferably, a thread angle φ of primary thread 212 (i.e., primary thread angle) is substantially the same as that of each of secondary threads 214 (i.e., secondary thread angle), although the primary thread angle and the secondary thread angle can be different. Each of the primary thread angle and the secondary thread angle is an acute angle of less than 45 degrees, and preferably 30 degrees. Primary thread 212 is represented by a plurality of crests 216. Each of secondary threads 214 is represented by a plurality of crests 218. The distance between every adjacent pair of crests 218 and 216 along a longitudinal axis 220 of dental implant 200, substantially equals to P/2. Secondary thread 214 ends with an intermediate screw turn 222, whose major diameter gradually reduces from $D_1$ to $D_3$. Alternatively, the major diameter of intermediate screw reduces from $D_1$ to $D_2$.

The jawbone (i.e., either the mandible or maxilla) of the patient includes a cortical bone below the gingiva, and a cancellous (spongy) bone below the cortical bone. The cortical bone is a substantially compact and solid bone, whereas the cancellous bone is porous and includes voids (similar to a sponge), and is not as strong as the cortical bone. Therefore, when a screw is tapped into the cortical bone and the cancellous bone of the jawbone, an upper portion of the screw which is located in the cortical bone, provides significant bonding that carries most of the load, while the lower portion of the screw which is located in the cancellous bone provides bonding of lesser significance.

The proof strength of a bolt which is tightened into a nut, in terms of tension and torque, is proportional to the stress area (i.e., the total surface area of those screw threads of the bolt which are in contact with the screw threads of the nut). Therefore, the greater the stress area, the greater the tensile load and the torque which the bolt can carry. The disclosed technique employs a screw whose coarsely threaded portion 210, which is located in the cancellous bone, has a stress area which is greater than that of finely threaded portion 208, which is located in the cortical bone. As the dental surgeon screws dental implant 200 into the jawbone, dental implant 200 compresses the cancellous bone surrounding the coarsely threaded portion of dental implant 200, thus strengthening the anchoring of dental implant 200 to the jawbone and expediting bone growth around dental implant 200. Therefore, the screw thread profile according to the disclosed technique provides a dental implant which has a proof strength substantially greater than that of a dental implant whose screw thread is uniform.

According to formula (1), minor diameter $D_2$ is smaller than minor diameter $D_3$. Therefore, the stress area of coarsely threaded portion 210 is greater than that of finely threaded portion 208. It is noted that the large thread height of primary thread 212 is larger than that of each of secondary threads 214. It is further noted, that since the pitch of primary thread 212 is substantially the same as that of each of secondary threads 214, after tapping a thread in the cortical bone by primary thread 212, each of secondary threads 214 carves and thus taps into a screw thread in parallel to the one formed by primary thread 212, in the cortical bone.

Dental implant 200 can include one or more longitudinal grooves (not shown), on a periphery thereof, disposed along longitudinal axis 220. Each of the longitudinal grooves can be located either on primary thread 212, each of secondary threads 214, or both primary thread 212 and secondary threads 214. While the dental surgeon screws dental implant 200 into the jawbone, bone particles which are produced due to the screwing action of primary thread 212 and secondary threads 214 into the jawbone, are deposited in the longitudinal grooves. In this manner, the longitudinal grooves serve as a depository for the bone particles. During the healing process, bone cells grow into the longitudinal grooves. Therefore, the longitudinal grooves provide an anchoring function in addition to that provided by primary thread 212 and secondary threads 214.

Figure 8:
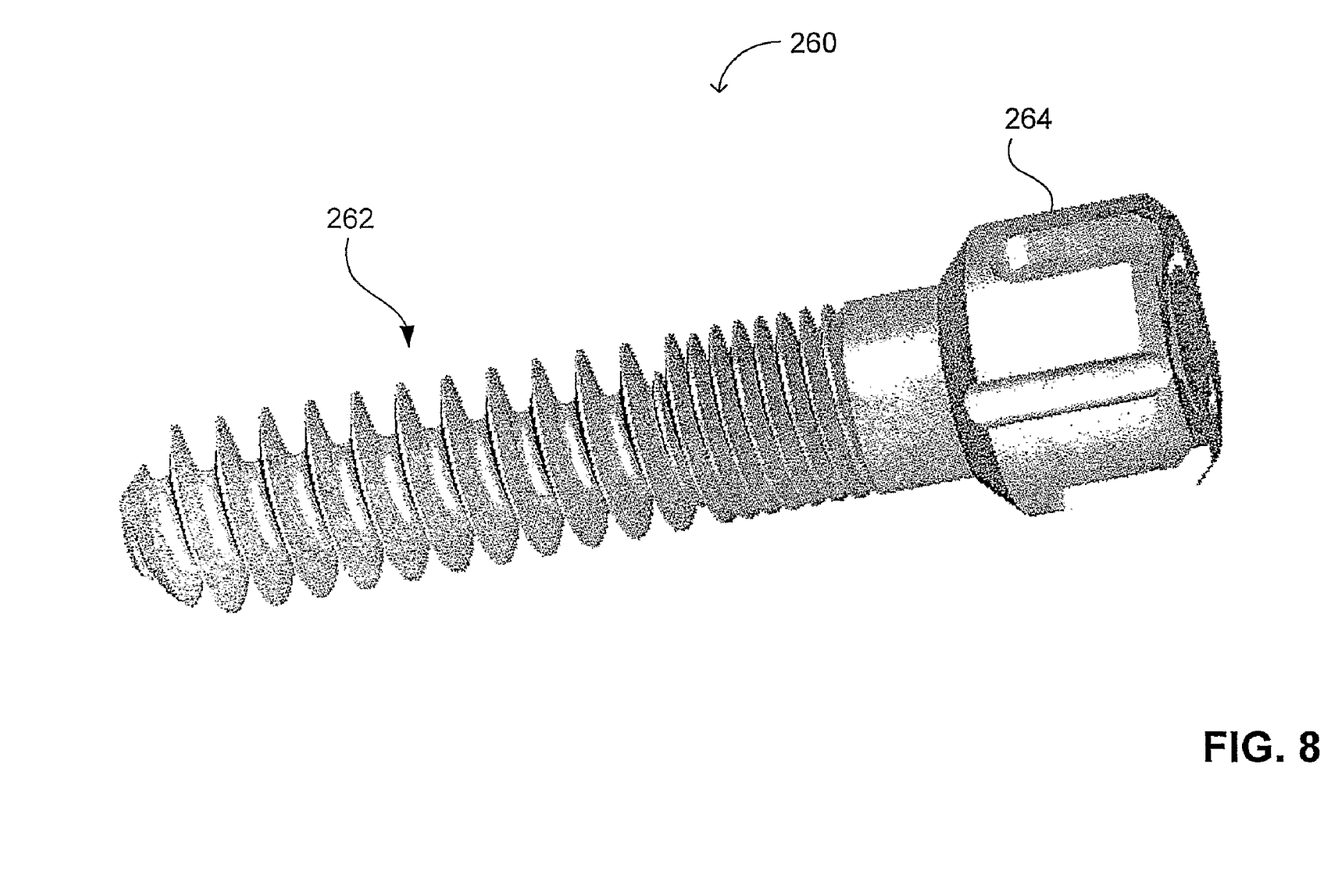
FIG. 8 is a schematic illustration of a perspective view of a device, for implanting an artificial tooth other than a slanted artificial incisor, in the jawbone of a patient, constructed and operative according to a further embodiment of the disclosed technique.
Figure 9A:
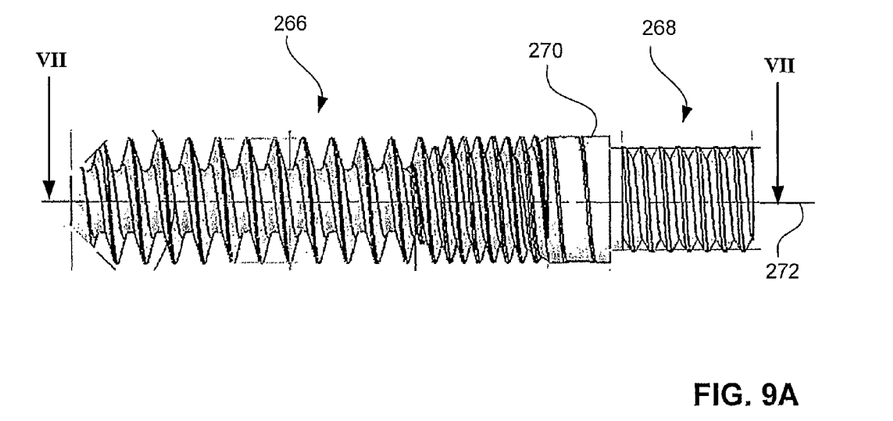
FIG. 9A is a schematic illustration of the dental implant of the device of FIG. 8.
Figure 9B:
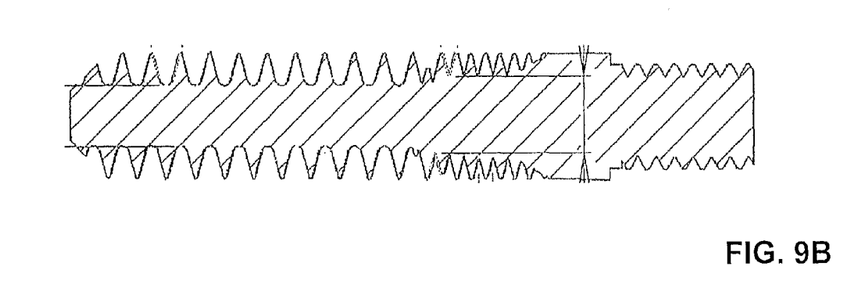
FIG. 9B is a schematic illustration of a section of the dental implant of FIG. 9A.
Figure 10A:
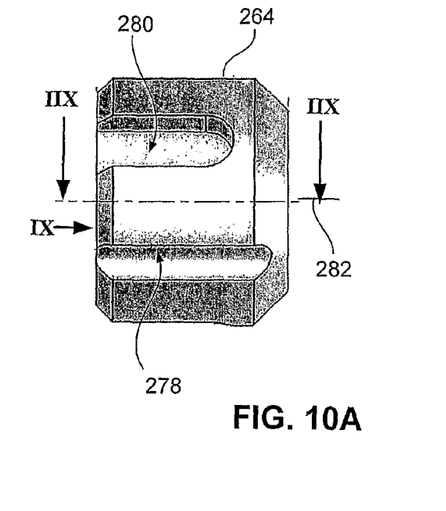
FIG. 10A is a schematic illustration of the deformably removable nut of the device of FIG. 8.
Figure 10B:
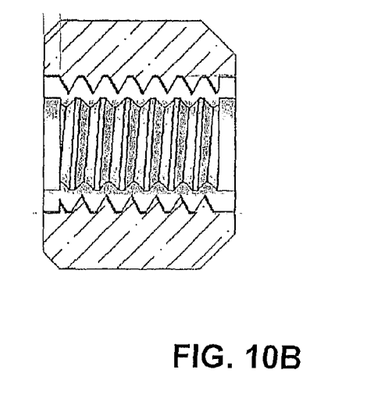
FIG. 10B is a schematic illustration of a section of the deformably removable nut of FIG. 10A.
Figure 10C:
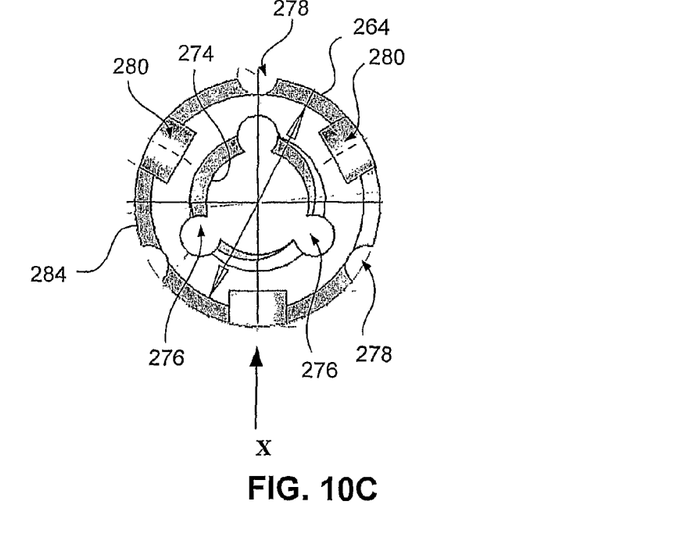
FIG. 10C is a schematic illustration of a side view of the deformably removable nut of FIG. 10A.
Figure 10D:
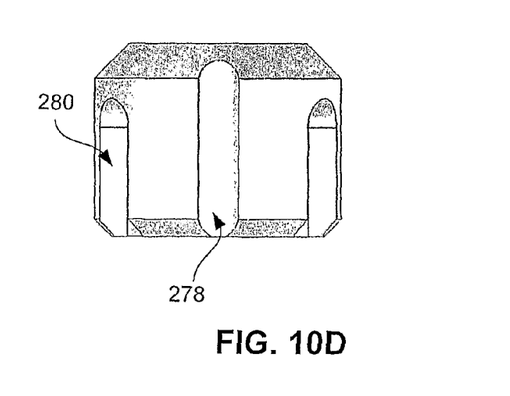
FIG. 10D is a schematic illustration of a side view of the deformably removable nut of FIG. 10C.
Figure 11:
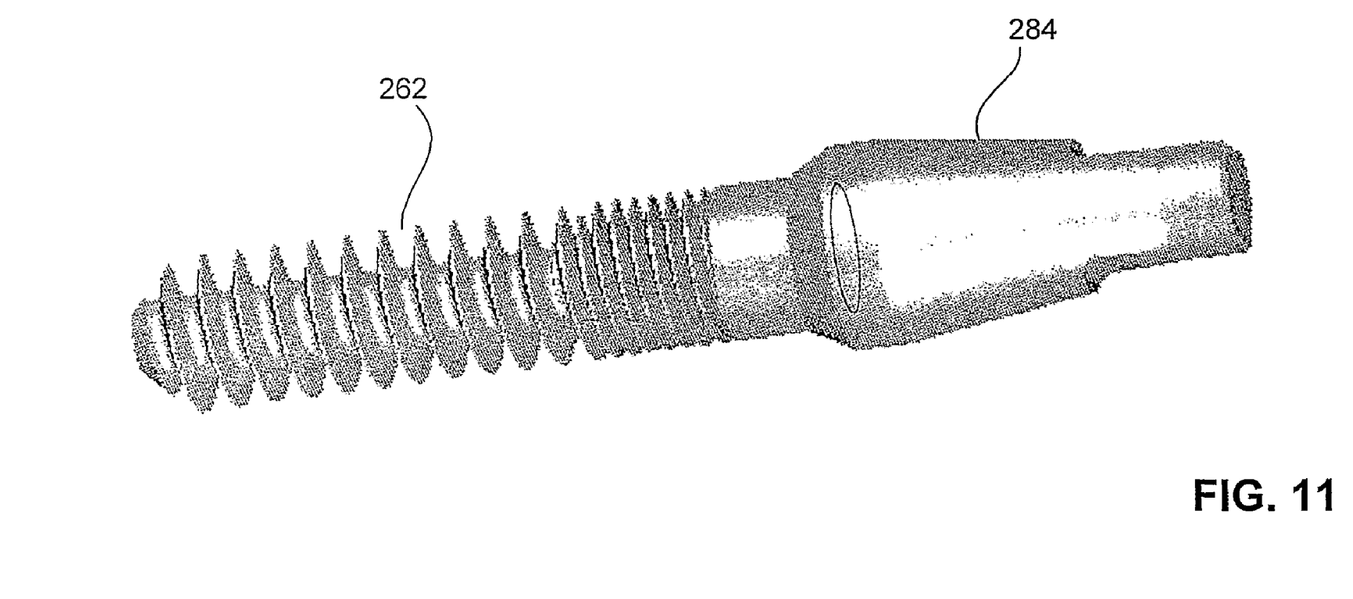
FIG. 11 is a schematic illustration of a perspective view of the artificial tooth coupler of FIG. 4A, screwed on the assembly stage portion of the dental implant of FIG. 9A.

Reference is now made to FIGS. 8, 9A, 9B, 10A, 10B, 10C, 10D, and 11. FIG. 8 is a schematic illustration of a perspective view of a device generally referenced 260, for implanting an artificial tooth other than a slanted artificial incisor, in the jawbone of a patient, constructed and operative according to a further embodiment of the disclosed technique. FIG. 9A is a schematic illustration of the dental implant of the device of FIG. 8. FIG. 9B is a schematic illustration of a section (i.e., section VII) of the dental implant of FIG. 9A. FIG. 10A is a schematic illustration of the deformably removable nut of the device of FIG. 8. FIG. 10B is a schematic illustration of a section (i.e., section IIX) of the deformably removable nut of FIG. 10A. FIG. 10C is a schematic illustration of a side view (i.e., view IX) of the deformably removable nut of FIG. 10A. FIG. 10D is a schematic illustration of a side view (i.e., view X) of the deformably removable nut of FIG. 10C. FIG. 11 is a schematic illustration of a perspective view of the artificial tooth coupler of FIG. 4A, screwed on the assembly stage portion of the dental implant of FIG. 9A.

With reference to FIG. 8, device 260 includes a dental implant 262, and a deformably removable nut 264. With reference to FIGS. 9A, and 9B, dental implant 262 includes a bone engaging portion 266 and an assembly stage portion 268. Bone engaging portion 266 and assembly stage portion 268 are similar to bone engaging portion 106 (FIG. 2A) and assembly stage portion 108, respectively, as described herein above. Dental implant 262 can include a screw stop portion 270, similar to screw stop portion 130 (FIG. 2A) as described herein above. Dental implant 262 is similar to dental implant 102 as described herein above in connection with FIG. 2A, except that bone engaging portion 266 and assembly stage portion 268, share the same longitudinal axis 272 (FIG. 9A).

With reference to FIG. 10C, deformably removable nut 264 includes an internal thread 274, a plurality of internal nut-disintegration features 276, a plurality of external nut-disintegration features 278, and a plurality of engagement features 280. Internal thread 274, internal nut-disintegration features 276, external nut-disintegration features 278, and engagement features 280, are similar to internal thread 112 (FIG. 3B), internal nut-disintegration feature 114, external nut-disintegration feature 116, and engagement features 118, respectively, as described herein above. In the example set forth in FIG. 10C, every pair of internal nut-disintegration features 276 and external nut-disintegration features 278 are equally distributed about a longitudinal axis 282 of deformably removable nut 264, on internal thread 274 and a periphery 284 of deformably removable nut 264. Deformably removable nut 264 is similar to deformably removable nut 104 (FIG. 3B), except that internal thread 274 and deformably removable nut 264, share the same longitudinal axis 282.

The dental surgeon follows the same procedure as that described herein above in connection with FIGS. 1, 2A, 2B, 3A, 3B, 3C, 4A, 4B, and 5, in order to implant dental implant 262, in the jawbone. With reference to FIG. 11, the dental surgeon screws an artificial tooth coupler 284 on assembly stage portion 268 (FIG. 9A) of dental implant 262. Artificial tooth coupler 284 is similar to artificial tooth coupler 124 (FIG. 4A), as described herein above.

It will be appreciated by persons skilled in the art that the disclosed technique is not limited to what has been particularly shown and described hereinabove. Rather the scope of the disclosed technique is defined only by the claims, which follow.

The invention claimed is:

1. A device for coupling an artificial tooth to a jawbone of a patient, the device comprising:
   a dental implant comprising:
   a threaded bone-engaging portion, for engaging said dental implant with said jawbone; and
   a threaded assembly-stage portion, for enabling screwing of said dental implant into said jawbone, and for coupling said artificial tooth with said jawbone; and
   a deformably removable nut comprising:
   a plurality of engagement features to enable engagement of said nut with a tool, for screwing said nut on said dental implant, and for further screwing said dental implant in said jawbone, with the aid of said nut; and
   a nut-disintegration feature to enable removal of said nut from said dental implant, without unscrewing said nut from said threaded assembly-stage portion.

2. The device according to claim 1, wherein said threaded assembly-stage portion is in form of an external thread.

3. The device according to claim 1, wherein a threaded assembly-stage longitudinal axis of said threaded assembly-stage portion, is slanted at a predetermined angle, from a threaded bone-engaging longitudinal axis of said threaded bone-engaging portion.

4. The device according to claim 1, wherein a threaded assembly stage longitudinal axis of said threaded assembly-stage portion, is substantially located on a threaded bone-engaging longitudinal axis of said threaded bone-engaging portion.

5. The device according to claim 1, wherein a thread profile of said threaded assembly-stage portion is substantially identical with that of said threaded bone-engaging portion.

6. The device according to claim 1, wherein a thread profile of said threaded assembly-stage portion is different than that of said threaded bone-engaging portion.

7. The device according to claim 1, wherein said nut-disintegration feature comprises at least one configuration selected from the group consisting of:
   internal; and
   external.

8. The device according to claim 1, wherein said nut-disintegration feature comprises at least on feature selected from the group consisting of:
   groove;
   notch;
   polygonal depression;
   perforated line in a wall of said deformably removable nut;
   hole; and
   slit.

9. The device according to claim 1, wherein said nut-disintegration feature runs from a distal end of said deformably removable nut to a proximal end of said deformably removable nut, substantially along a nut longitudinal axis of said deformably removable nut.

10. The device according to claim 1, wherein said nut-disintegration feature runs from a distal end of said deformably removable nut to a proximal end of said deformably removable nut, at an angle slanted to a nut longitudinal axis of said deformably removable nut.

11. The device according to claim 1, wherein said deformably removable nut further comprises an internal thread for enabling coupling of said deformably removable nut with said dental implant, by screwing said deformably removable nut on said threaded assembly-stage portion.

12. The device according to claim 11, wherein said nut-disintegration feature is configured both internal and external, defining a disintegration wall thickness thinner than a nut wall thickness defined between said internal thread and an outer wall of said deformably removable nut.

13. The device according to claim 11, wherein a thread longitudinal axis of said internal thread, is slanted from a nut longitudinal axis of said deformably removable nut.

14. The device according to claim 11, wherein a thread longitudinal axis of said internal thread, is substantially located on a nut longitudinal axis of said deformably removable nut.

15. The device according to claim 11, wherein said nut-disintegration feature is configured internal, and
   wherein a disintegration wall thickness defined by a nut material between said nut-disintegration feature and an outer wall of said deformably removable nut, is thinner than a nut wall thickness defined between said internal thread and said outer wall.

16. The device according to claim 11, wherein said nut-disintegration feature is configured external, and wherein a disintegration wall thickness defined by a nut material between said nut-disintegration feature and an outer wall of said deformably removable nut, is thinner than a nut wall thickness defined between said internal thread and said outer wall.

17. The device according to claim 1, wherein said deformably removable nut is uncoupled from said dental implant, by employing at least one feature selected from the group consisting of:
chemical substance which dissolves the material of said deformably removable nut; and
heat.

18. The device according to claim 1, wherein each of said engagement features is in form of a depression in an outer wall of said deformably removable nut.

19. The device according to claim 1, wherein each of said engagement features is in form of a protrusion from an outer wall of said deformably removable nut.

20. The device according to claim 1, wherein said dental implant further comprises a screw stop located between said threaded bone-engaging portion and said threaded assembly-stage portion, to prevent advancement of said deformably removable nut past said screw stop, when said deformably removable nut is screwed on said threaded assembly-stage portion.

21. The device according to claim 1, wherein said threaded bone-engaging portion comprises:
a finely threaded portion located at an implant proximal end of said threaded bone-engaging portion; and
a coarsely threaded portion located at an implant distal end of said threaded bone-engaging portion.

22. The device according to claim 21, wherein a coarsely threaded distal end of said coarsely threaded portion, is in form of a truncated cone.

23. The device according to claim 21, wherein a finely threaded minor diameter of said finely threaded portion, is greater than a coarsely threaded minor diameter of said coarsely threaded portion.

24. The device according to claim 21, wherein said threaded bone-engaging portion comprises:
a primary thread which runs along said finely threaded portion, and said coarsely threaded portion; and
a plurality of secondary threads which run along said finely threaded portion,
wherein a coarse thread height of said primary thread, is greater than a fine thread height of each of said secondary threads,
wherein a coarse pitch value of a coarse pitch of said primary thread, is substantially equal to a fine pitch value of a fine pitch of each of said secondary threads,
wherein each of said secondary threads runs in a direction substantially parallel with that of said primary thread, at an offset whose value is substantially equal to a quotient of said fine pitch value, and a sum of the quantity of said secondary threads, and tile numerical value of one,
wherein a primary thread angle value of said primary thread, is substantially equal to a secondary thread angle value of each of said secondary threads,
wherein a crest distance value of a crest distance between every adjacent pair of a plurality of crests of said primary thread and each of said secondary threads, along a threaded bone-engaging longitudinal axis of said threaded bone-engaging portion, is substantially equal to half of said fine pitch value,
wherein said secondary threads include an intermediate screw turn, located between said secondary threads and said primary thread, and
wherein an intermediate major diameter value of an intermediate major diameter of said intermediate screw turn, gradually reduces from a coarse major diameter value of a coarse major diameter of said primary thread, to a coarse minor diameter value of a coarse minor diameter of said primary thread.

25. The device according to claim 24, wherein said primary thread angle value is different than said secondary thread angle value.

26. The device according to claim 24, wherein said intermediate major diameter value gradually reduces from said coarse major diameter value, to a fine minor diameter value of a fine minor diameter of each of said secondary threads.

27. The device according to claim 24, wherein said dental implant further includes a plurality of longitudinal grooves located on a periphery of at least one of said primary thread, and said secondary threads.

28. A device for coupling an artificial tooth to a jawbone of a patient, the device comprising:
a dental implant comprising:
a threaded bone-engaging portion, for engaging said dental implant with said jawbone; and
a threaded assembly-stage portion, for enabling screwing of said dental implant into said jawbone, and for coupling said artificial tooth with said jawbone; and
a deformably removable nut comprising:
a plurality of engagement features to enable engagement of said nut with a tool, for screwing said nut on said dental implant, and for further screwing said dental implant in said jawbone, with the aid of said nut; and
a nut-disintegration feature to enable removal of said nut from said dental implant, without unscrewing said nut from said threaded assembly stage portion; and
an artificial tooth coupler having an internal thread compatible with said threaded assembly-stage portion, said artificial tooth coupler being coupled to said dental implant, by screwing said artificial tooth coupler on said threaded assembly-stage portion, said artificial tooth coupler having a protruding portion, for coupling said artificial tooth thereto.

* * * * *